United States Patent
Amalric et al.

[11] Patent Number: 5,888,482
[45] Date of Patent: Mar. 30, 1999

[54] EMULSIFYING COMPOSITION BASED ON ALKYLPOLYGLYCOSIDES AND ITS USES

[75] Inventors: Chantal Amalric, Blan; Nelly Michel, Maisons Alfort, both of France

[73] Assignee: Societe d'Exploitation de Produits Pour l'Industrie Chimique SEPPIC, Paris Cedex, France

[21] Appl. No.: 687,614

[22] PCT Filed: May 24, 1996

[86] PCT No.: PCT/FR96/00782

§ 371 Date: Oct. 3, 1996

§ 102(e) Date: Oct. 3, 1996

[87] PCT Pub. No.: WO96/37285

PCT Pub. Date: Nov. 28, 1996

[30] Foreign Application Priority Data

May 24, 1995 [FR] France ................................. 95 06234

[51] Int. Cl.⁶ .............................. A61K 7/42; B01F 17/38; B01F 17/56; B01J 13/00
[52] U.S. Cl. ........................... 424/59; 424/401; 514/938; 514/939; 514/975; 516/72; 516/917
[58] Field of Search .................................. 252/312, 351; 424/59; 514/938, 939, 975

[56] References Cited

U.S. PATENT DOCUMENTS

| | | | |
|---|---|---|---|
| 2,942,008 | 6/1960 | Lubowe | ................................. 252/364 |
| 3,547,828 | 12/1970 | Mansfield et al. | ...................... 252/351 |
| 4,740,367 | 4/1988 | Force et al. | .......................... 514/938 X |
| 4,919,923 | 4/1990 | Hoeffkes et al. | .................... 514/938 X |
| 5,268,126 | 12/1993 | Balzer | ..................................... 252/312 |
| 5,494,938 | 2/1996 | Kawa et al. | ......................... 514/938 X |
| 5,510,100 | 4/1996 | Picard et al. | ............................... 424/59 |
| 5,556,573 | 9/1996 | Weuthen et al. | ..................... 252/351 X |

FOREIGN PATENT DOCUMENTS

WO92/06778  4/1992  WIPO .
WO95/13863  5/1995  WIPO .

*Primary Examiner*—Richard D. Lovering
*Attorney, Agent, or Firm*—Young & Thompson

[57] ABSTRACT

An emulsifying composition comprising from 10 to 40 weight % of a mixture of alkylpolyglycosides and from 90 to 60 weight % of at least one fatty alcohol of formula R'OH, where R' is a saturated or unsaturated alkyl radical having from 12 to 18 carbon atoms, where the mixture of alkylpolyglycosides comprises:

$$R_1O(G_1)X_1 \qquad (I)$$

in which $R_1$ is a saturated or unsaturated alkyl radical having 12 or 14 carbon atoms, $G_1$ is the residue of a sugar and $X_1$ is between 1 and 5;

(ii) an alkylpolyglycoside of formula (II)

$$R_2O(G_2)X_2 \qquad (II)$$

in which $R_2$ is a saturated or unsaturated alkyl radical having 16 carbon atoms, $G_2$ is the residue of a sugar and $X_2$ is between 1 and 5; and (iii) an alkylpolyglycoside of formula (III)

$$R_3O(G_3)X_3 \qquad (III)$$

in which $R_3$ is a saturated or unsaturated alkyl radical having 18 carbon atoms, $G_3$ is the residue of a sugar and $X_3$ is between 1 and 5, the ratio by weight of the alkylpolyglycosides of formula (I) to the alkylpolyglycosides of formulae (II) and (III) being between 0.4 and 5. The emulsifying composition is useful as self-emulsifiable agent for the preparation of an emulsion.

14 Claims, No Drawings

EMULSIFYING COMPOSITION BASED ON ALKYLPOLYGLYCOSIDES AND ITS USES

CROSS-REFERENCES TO RELATED APPLICATION

This application is the 35 USC 371 National stage application of International application PCT/FR96/00782, filed May 24, 1996, which designated the United States of America.

FIELD OF THE INVENTION

The present invention relates to an emulsifying composition comprising a mixture of alkylpolyglycosides and at least one fatty alcohol, to the use of these compositions as self-emulsifiable compositions for the preparation of emulsions and to emulsions comprising such an emulsifying composition.

BACKGROUND OF THE INVENTION

It is well known to prepare emulsions, in particular in the cosmetics and dermatological field, by means of hydrophilic-type nonionic surfactants obtained by grafting a polyoxyethylene chain. These emulsifying nonionic surfactants can be provided in the form of compositions based on alcohols, on acids or on fatty esters which have the advantage of being self-emulsifiable. "Self-emulsifiable" is understood to mean, in this instance, a composition which makes it possible to obtain a stable emulsion by simple mixing with an aqueous phase with moderate stirring.

The nonionic surfactants comprising a polyoxyethylene chain mentioned above have the disadvantage, however, of being irritating to a greater or lesser extent. Moreover, it was possible to find that the emulsions prepared with these self-emulsifying compositions were stable for only a relatively short period of time.

For the purpose of overcoming these disadvantages, the Applicant Company has provided, in Application WO-92/06778, for the use of self-emulsifiable compositions based on fatty alcohols and on alkylpolyglycosides or alkylpolysaccharides. Self-emulsifiable compositions as described in the abovementioned application are sold by the company S.E.P.P.I.C. under the tradename Montanov®68. The latter contain a mixture of alkylpolyglycosides, the fatty chains of which comprise 16 and 18 carbon atoms, and a mixture of fatty alcohols with the same fatty chain length.

The Applicant Company has, however, recently found that emulsifying compositions which are useful as self-emulsifiable compositions, of the Montanov®68 type, could result in emulsions being obtained which have little stability when they are subjected to low, indeed very low, temperatures, for example temperatures lower than approximately −20° C. Some users of these emulsifying compositions want the emulsions which they prepare to be stable even at temperatures of this order.

Emulsifying compositions are consequently provided, by the present invention, which make it possible to obtain emulsions which are stable at low temperatures, for example temperatures of less than −20° C. These emulsifying compositions, moreover, do not exhibit the disadvantage of the compositions based on polyoxyethylene compounds mentioned above. More particularly, these emulsifying compositions according to the invention are not irritating. In addition, the emulsifying compositions according to the invention can be used as self-emulsifiable compositions.

SUMMARY OF THE INVENTION

The first subject of the present invention is therefore an emulsifying composition comprising from 10 to 40 weight % of a mixture of alkylpolyglycosides and from 90 to 60 weight % of at least one fatty alcohol of formula R'OH, where R' is a linear or branched, saturated or unsaturated aliphatic radical having from 12 to 18 carbon atoms, characterized in that the mixture of alkylpolyglycosides comprises:

(i) at least one alkylpolyglycoside of formula (I):

$$R_1O(G_1)X_1 \qquad (I)$$

in which $R_1$ is a linear or branched aliphatic radical having 12 or 14 carbon atoms, $G_1$ is the residue of a sugar and $X_1$ is between 1 and 5;

(ii) an alkylpolyglycoside of formula (II)

$$R_2O(G_2)X_2 \qquad (II)$$

in which $R_2$ is a linear or branched aliphatic radical having 16 carbon atoms, $G_2$ is the residue of a sugar and $X_2$ is between 1 and 5;

(iii) an alkylpolyglycoside of formula (III)

$$R_3O(G_3)X_3 \qquad (III)$$

in which $R_3$ is a linear or branched aliphatic radical having 18 carbon atoms, $G_3$ is the residue of a sugar and $X_3$ is between 1 and 5, and the ratio by weight of the alkylpolyglycosides of formula (I) to the alkylpolyglycosides of formulae (II) and (III) being between 0.4 and 5.

"Fatty alcohol of formula R'OH" is understood to mean an alcohol derived from a fatty acid, whether this is a natural fatty acid or whether it is obtained by chemical synthesis. It can, in particular, be derived from octanoic, decanoic, dodecanoic, tetradecanoic, hexadecanoic, octadecanoic, eicosanoic, docasanoic, octadecenoic, eicasenoic, octodecadienic or octadecatrienic acids.

According to an advantageous characteristic, the ratio by weight of the alkylpolyglycosides of formula (I) to the alkylpolyglycosides of formulae (II) and (III) is between 0.5 and 1.5.

$G_1$, $G_2$ and $G_3$, which are identical or different, can represent the residue of a sugar chosen from dextrose, sucrose, fructose, galactose, maltose, maltotriose, lactose, cellobiose, mannose, ribose, dextran, thalose, allose, xylose, levoglucosan, cellulose and starch. The residue of the sugar is preferably a glucose or fructose residue. Very preferentially, $G_1$, $G_2$ and $G_3$ are identical and each represent the residue of a glucose.

The alkylpolyglycosides of formulae (I), (II) and (III) have a value of $x_1$, $x_2$ and $x_3$, which are identical or different, of between 1.1 and 2.

According to another advantageous aspect of the invention, the emulsifying composition comprises an alkylpolyglycoside of formula (I) where $R_1$ is an aliphatic radical comprising 12 carbon atoms and an alkypolyglycoside of formula (I) where $R_1$ is an aliphatic radical comprising 14 carbon atoms. Moreover, $R_2$ and $R_3$ are alkyl radicals, such that $R_2$ represents a palmityl radical and $R_3$ represents a stearyl radical. The ratio by weight of the alkylpolyglycosides of formula (II) to the alkylpolyglycosides of formula (III) is generally between 10/90 and 90/10, preferably between 30/70 and 70/30.

The emulsifying composition according to the invention generally comprises a number of fatty alcohols of formula R'OH, as defined above. These fatty alcohols are provided in the form of a mixture containing:

(i) at least one fatty alcohol comprising 12 or 14 carbon atoms, preferably a fatty alcohol comprising 12 carbon atoms and a fatty alcohol comprising 14 carbon atoms;

(ii) a fatty alcohol comprising 16 carbon atoms and a fatty alcohol containing 18 carbon atoms.

The fatty alcohols present in the emulsifying composition comprise an alkyl radical R' which is preferably saturated.

The ratio by weight of the fatty alcohols comprising 12 or 14 carbon atoms to the fatty alcohols comprising 16 and 18 carbon atoms is generally between 0.03 and 0.1.

According to another aspect, the invention also relates to an emulsion comprising at least one aqueous phase and one oil phase, said emulsion comprising an emulsifying composition according to the invention, as defined above.

The constituent oil phase of the emulsion can be composed of an oil chosen from the following oils:

oils of plant origin, such as sweet almond oil, coconut oil, castor oil, jojoba oil, olive oil, rapeseed oil, groundnut oil, hazelnut oil, palm oil, karite butter, apricot kernel oil or calophyllum oil;

oils of animal origin, such as perhydrosqualene;

mineral oils, such as liquid paraffin, liquid petrolatum and mineral oils, in particular resulting from petroleum fractions, having a boiling point of between 300° and 400° C.;

synthetic oils, such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, isoparaffins and silicone oils. Mention may more particularly be made, among the latter, of dimethylpolysiloxanes, methylphenylpolysiloxanes, amino-modified silicone amines, silicones modified by fatty acids, silicones modified by alcohols, silicones modified by alcohols and fatty acids, silicones modified by polyether groups, epoxy-modified silicones, silicones modified by fluorinated groups, cyclic silicones and silicones modified by alkyl groups.

These emulsions can be prepared by dispersion while hot, for example at a temperature of between 50° and 80° C., of an emulsifying composition according to the invention in water or in a polar solvent; this dispersion being produced by simple slow stirring, in particular mechanical stirring.

When the emulsion comprises an oil as defined above, the latter can be melted with the emulsifying composition according to the invention, at a temperature of between 50° and 80° C. The mixture obtained is then dispersed in water or the polar solvent, brought to a temperature of between 50° and 80° C.

An emulsion according to the invention generally comprises from 1 to 10 weight % of the emulsifying composition defined above.

According to another aspect, the invention relates to the use of an emulsifying composition as self-emulsifiable agent for the preparation of a stable emulsion, in particular an emulsion which is stable at less than −20° C., said emulsifying composition and said emulsion being as defined above.

Another subject of the invention is the use of emulsions thus prepared in human or animal bodily hygiene and the creams thus prepared for the implementation of a method for the preventive or symptomatic treatment of cutaneous conditions of the human or animal body related to exposure to sunlight.

DETAILED DESCRIPTION OF THE INVENTION

The aim of the following examples is to illustrate the present invention.

EXAMPLE 1

Process for the Preparation of an Emulsifying Composition According to the Invention A fatty alcohol fraction is introduced into a multipurpose reactor, the fraction having the following composition (weight %):

lauryl alcohol ($C_{12}$) 12.5% myristyl alcohol ($C_{14}$) 17.5% palmityl alcohol ($C_{16}$) 29.0% stearyl alcohol ($C_{18}$) 41.0%

Glucose is also introduced into the reactor so that the molar ratio of the fatty alcohols to the glucose is 6:1. The glucose is then reacted with the fatty alcohols for 5 hours at a temperature of between 100° and 105° C., in the presence of sulfuric acid as catalyst. The reaction is carried out under a partial vacuum of 15 mm of mercury (2 kPa).

The composition obtained comprises 75.5% of free fatty alcohols in the following contents (weight %):

as $C_{12}$ 9.5 as $C_{14}$ 13.0 as $C_{16}$ 22.0 as $C_{18}$ 31.0

After reaction, the catalyst is neutralized with a base. The $C_{12}$ and $C_{14}$ alcohols present in the reaction mixture are partially removed by distillation on a thin-film evaporator. Fatty alcohols comprising 16 and 18 carbon atoms are added to the reaction mixture for the purpose of obtaining the desired composition.

The composition obtained comprises:

free fatty alcohols (weight %):

as $C_{12}$ ≦1.2 as $C_{14}$ ≦2.0 as $C_{16}$ 26.0 as $C_{18}$ 36.0 alkylpolyglucosides (weight %):

as $C_{12}$ 5.76 as $C_{14}$ 7.44 as $C_{16}$ 9.60 as $C_{18}$ 13.2

EXAMPLE 2

Process for the Preparation of an Emulsifying Composition According to the Invention For the purpose of preparing an emulsifying composition according to the invention, a composition 2 and a composition 3 were mixed, each being based on a mixture of alkylpolyglucosides and of free fatty alcohols.

The composition 2 was prepared according to the process described in International Application WO-92/06778. This composition 2 comprised (weight %):

$C_{16}$ alkylpolyglucosides 10.0%

$C_{18}$ alkylpolyglucosides 10.0% cetylstearil [sic] alcohol 80.0%

The composition 3 was prepared by reaction of glucose with a suitable mixture of alcohols, according to the process described in Example 3 of International Application PCT/FR/94/01336, filed on 16 Nov. 1994, in the name of S.E.P.P.I.C. More specifically, this composition 3 comprised (weight %):

$C_{12}$ alkylpolyglucosides 14.4%

$C_{14}$ alkylpolyglucosides 18.6%

$C_{16}$ alkylpolyglucosides 9.0%

$C_{18}$ alkylpolyglucosides 18.0% lauryl alcohol 3.0% myristyl alcohol 4.0% palmityl alcohol 6.0% stearyl alcohol 27.0%

The compositions 2 and 3 were provided in solid form. They were melted together at 70° C., in proportions appropriate for obtaining an emulsifying composition according to the invention identical in its constituents and their relative proportions to that obtained in Example 1 above.

EXAMPLE 3

Sun Cream

A sun cream is prepared which comprises the following compounds (weight %):

*phase A):
 emulsifying composition of Example 2 5.0%
 dimethicone 5.0%
 cyclomethicone 10.0%
 3-benzophenone 0.5%
 octyl para-methoxycinnamate 5.0%

*phase B):
 sepicide HB[(1)] 0.5%
[(1)]: preservative sold by the company S.E.P.P.I.C.
 sepicide Cl[(2)] 0.2%
[(2)]: preservative sold by the company S.E.P.P.I.C.
 fragrances 0.1%

*phase C):
 water q.s. for 100%

The sun cream is obtained in the following way:

the phase A) is melted at 70° C.;

the phase C) is heated to 75° C.;

the phase A) is mixed with the phase C) with moderate stirring to form an emulsion;

the phase B) is introduced into the emulsion formed, when the temperature of the latter reaches 40° C.;

the pH is adjusted to 6, if necessary.

The emulsion obtained has the appearance of a glossy white cream. Its viscosity is 25,000 mpa·s (Brookfield LVF, model IV, six revolutions/min.).

For the purpose of assessing the stability towards cold of the emulsion obtained, it was subjected to the following test:

the emulsion was packaged in two 30 ml glass bottles. One of these bottles is frozen at −26° C. whereas the other bottle (control emulsion) is stored at room temperature. The emulsion contained in the latter bottle is used as reference.

The emulsion tested is placed at −26° C. for 18 hours and then spontaneously unfrozen at room temperature for 6 hours. The test emulsion and the control emulsion then form the subject of a comparative visual inspection and are graded in the following way:

0: the test emulsion is comparable with the control emulsion as regards its homogeneous, smooth and glossy appearance.

X: the test emulsion exhibits a matt and less smooth surface than the control emulsion.

XX: the test emulsion exhibits a markedly granular* surface with loss of glossiness, a characteristic and easily identifiable appearance even without reference to the control emulsion.

*The appearance is granular but the physical presence of grains is not recorded when the emulsion is spread; it relates solely to visual monitoring and visual assessment.

XXX: the test emulsion is destructured and exudation of water is found at the surface.

The sun cream obtained according to the process described above, subjected to the cold test, as defined above, was graded.

EXAMPLE 4

Cream Containing Vegetable Oils

A cream containing vegetable oils was prepared which comprises the following compounds (weight %):

*phase A):
 emulsifying composition of Example 2 5.0%
 jojoba oil 5.0%
 hazelnut oil 5.0%
 sweet almond oil 10.0%
 DL-α-tocopherol 0.05%

*phase B):
 sepicide HB[(1)] 0.3%
[(1)]: preservative sold by the company S.E.P.P.I.C.
 sepicide Cl[(2)] 0.2%
[(2)]: preservative sold by the company S.E.P.P.I.C.
 fragrances 0.4%

*phase C):
 water q.s. for 100%

The cream containing vegetable oils is prepared in the following way:

the phase A) is melted at 70° C.;

the phase C) is heated to 75° C.;

the phase A) is mixed with the phase C) with moderate stirring to form an emulsion;

the phase B) is introduced into the emulsion formed, when the temperature of the latter has reached approximately 40° C.;

the pH is adjusted to 6, if necessary.

The emulsion obtained has the appearance of a glossy ivory cream and its viscosity is 23,000 mPa·s (Brookfield LVF, model IV, six revolutions/min.).

This cream containing vegetable oils is subjected to the cold test described in Example 3 above. Visual inspection of the composition subjected to this test resulted in the latter being graded: 0

EXAMPLE 5

Different emulsions were prepared which comprise (weight %):

emulsifying composition based on alkylpolyglucosides and on fatty alcohols 5.0% oil 20% water q.s. for 100%

The emulsifying composition used was either that of Example 2 (composition 1) or the emulsifying composition 2 defined in Example 2 above.

The oils used were as follows:

Primol 352: liquid paraffin sold by the company Esso

Lanol 1688: cetearyl octanoate, sold by the company S.E.P.P.I.C.

sweet almond oil (SAO);

DC 200/350: dimethicone sold by the company Dow Corning.

The emulsions obtained were subjected to the cold test described in Example 3. The results obtained appear in Table 1 below:

TABLE 1

| Emulsifying composition | Oil | | | |
|---|---|---|---|---|
| | Primol 352 | Lanol 1688 | SAO | DC 200/350 |
| I | 0 | 0 | 0 | 0 |
| II | XXX | XXX | XXX | XXX |

The results obtained show that the compositions according to the invention are markedly more stable when they are subjected to low temperatures than emulsions according to the prior art.

We claim:

1. Emulsifying composition comprising from 10 to 40 weight % of a mixture of alkylpolyglycosides and from 90 to 60 weight % of a mixture of fatty alcohols of general formula R'OH, where R' is a saturated or unsaturated alkyl radical having from 12 to 18 carbon atoms, said mixture of fatty alcohols containing:

(i) at least one fatty alcohol comprising 12 or 14 carbon atoms, and (ii) a fatty alcohol comprising 16 carbon atoms, and a fatty alcohol containing 18 carbon atoms, and wherein the mixture of alkylpolyglycosides comprises:

(iii) at least one alkylpolyglycoside of formula (I):

    $$R_1O(G_1)X_1 \qquad (I)$$

in which $R_1$ is a linear or branched aliphatic radical having 12 or 14 carbon atoms, $G_1$ is the residue of a sugar and $X_1$ is between 1.1 and 2;

(iv) an alkylpolyglycoside of formula (II)

    $$R_2O(G_2)X_2 \qquad (II)$$

in which $R_2$ is a linear or branched aliphatic radical having 16 carbon atoms, $G_2$ is the residue of a sugar and $X_2$ is between 1.1 and 2; and (v) an alkylpolyglycoside of formula (III)

    $$R_3O(G_3)X_3 \qquad (III)$$

in which $R_3$ is a linear or branched aliphatic radical having 18 carbon atoms, $G_3$ is the residue of a sugar and $X_3$ is between 1.1 and 2, in which $G_1$, $G_2$ and $G_3$ represent, independently of one another, a fructose or glucose residue, in which the ratio of the fatty alcohols comprising 12 or 14 carbon atoms to the fatty alcohols comprising 16 and 18 carbon atoms is between 0.03 to 0.1, and the ratio by weight of the alkylpolyglycosides of formula (I) to the alkylpolyglycosides of formulae (II) and (III) being between 0.4 and 5.

2. Emulsifying composition according to claim 1, wherein the ratio by weight of the alkylpolyglycosides of formula (I) to the alkylpolyglycosides of formulae (II) and (III) is between 0.5 and 1.5.

3. Emulsifying composition according to claim 1, wherein $G_1$, $G_2$ and $G_3$ represent a glucose residue.

4. Emulsifying composition according to claim 1, comprising an alkylpolyglycoside of formula (I) where $R_1$ is an aliphatic radical comprising 12 carbon atoms and an alkylpolyglycoside of formula (I) where $R_1$ is an aliphatic radical comprising 14 carbon atoms.

5. Emulsifying composition according to claim 1, wherein $R_2$ represents a palmityl radical and $R_3$ represents a stearyl radical.

6. Emulsifying composition according to claim 1, wherein the ratio by weight of the alkylpolyglycoside of formula (II) to the alkylpolyglycoside of formula (III) is between 10/90 and 90/10.

7. Emulsifying composition according to claim 6, wherein the ratio by weight of the alkylpolyglycoside of formula (II) to the alkylpolyglycoside of formula (III) is between 30/70 and 70/30.

8. Emulsifying composition according to claim 1, comprising:

at most 1.2% of free $C_{12}$ fatty alcohols;

at most 2.0% of free $C_{14}$ fatty alcohols;

26% of free $C_{16}$ fatty alcohols;

36% of free $C_{18}$ fatty alcohols;

5.76% of $C_{12}$ alkylpolyglucosides;

7.44% of $C_{14}$ alkylpolyglucosides;

9.60% of $C_{16}$ alkylpolyglucosides;

13.20% of $C_{18}$ alkylpolyglucosides.

9. An emulsion comprising at least one aqueous phase and one oil phase, and an emulsifying composition according to claim 1.

10. An emulsion according to claim 9, wherein the oil phase comprises at least one compound selected from the group consisting of silicone oils, oils of plant origin, and liquid paraffin.

11. Sun cream containing:

the emulsifying composition according to claim 1 5% dimethicone 5% cyclomethicone 5%

3-benzophenone 0.5% octyl para-methoxycinnamate 5% a first preservative 0.5% a second preservative 0.2% fragrances 0.1% water q.s. for 100%.

12. Cream according to claim 11 for the implementation of a method for the preventive or curative treatment of cutaneous conditions of the human or animal body related to exposure to sunlight.

13. Cream containing vegetable oils containing:

*phase A):

emulsifying composition according to claim 8 5.0% jojoba oil 5.0% hazelnut oil. 5.0% sweet almond oil 10.0%

DL-α-tocopherol 0.05%

*phase B):

a first preservative 0.3% a second preservative 0.2% fragrances 0.4%

*phase C):

water q.s. for 100%.

14. Cream according to claim 13 for the implementation of a method for the preventive or curative treatment of cutaneous conditions of the human or animal body related to exposure to sunlight.

* * * * *